US008889946B2

(12) United States Patent
Hermansson et al.

(10) Patent No.: US 8,889,946 B2
(45) Date of Patent: Nov. 18, 2014

(54) MALE INCONTINENCE GUARD COMPRISING AN ABSORBENT BARRIER

(75) Inventors: Kent Hermansson, Västra Frölunda (SE); Carina Hedlund, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 9 days.

(21) Appl. No.: 13/805,901

(22) PCT Filed: Jun. 22, 2011

(86) PCT No.: PCT/SE2011/050822
§ 371 (c)(1),
(2), (4) Date: Dec. 20, 2012

(87) PCT Pub. No.: WO2011/162709
PCT Pub. Date: Dec. 29, 2011

(65) Prior Publication Data
US 2013/0096525 A1    Apr. 18, 2013

(30) Foreign Application Priority Data
Jun. 24, 2010  (SE) .................. PCT/SE2010/050731

(51) Int. Cl.
| *A61F 13/53* | (2006.01) |
| *A61F 13/56* | (2006.01) |
| *A61F 13/58* | (2006.01) |
| *A61F 13/514* | (2006.01) |
| *A61F 13/475* | (2006.01) |
| *A61F 13/515* | (2006.01) |
| *A61F 13/471* | (2006.01) |

(52) U.S. Cl.
CPC ........... *A61F 13/53* (2013.01); *A61F 13/51458* (2013.01); *A61F 13/4752* (2013.01); *A61F 13/515* (2013.01); *A61F 13/471* (2013.01)
USPC ............................ 604/369; 604/378; 604/374

(58) Field of Classification Search
CPC ......... A61F 13/00; A61F 13/53; A61F 13/56; A61F 13/58; A61F 13/15203
USPC ......................................... 604/369
See application file for complete search history.

(56) References Cited

U.S. PATENT DOCUMENTS

| 5,207,662 A | 5/1993 | James |
| 5,624,423 A | 4/1997 | Anjur et al. |

(Continued)

FOREIGN PATENT DOCUMENTS

| DE | 20 2007 005 479 | 8/2007 |
| EP | 0 091 412 | 10/1983 |
| EP | 0 167 931 | 1/1986 |
| EP | 1 136 051 | 9/2001 |
| EP | 1 184 013 | 3/2002 |

(Continued)

*Primary Examiner* — Tatyana Zalukaeva
*Assistant Examiner* — Sara Sass
(74) *Attorney, Agent, or Firm* — Drinker Biddle & Reath LLP

(57) ABSTRACT

A male incontinence guard includes a liquid permeable topsheet, a backsheet, and an absorbent body between the topsheet and the backsheet. The guard has a transverse direction and a longitudinal direction and is divided by a transverse dividing line into a front region with a front transverse edge and a rear region with a rear transverse edge. The front region has a greater maximum extension in the transverse direction than the maximum extension of the rear region in the transverse direction, and the longitudinal extension of the rear region is 10-60% of the longitudinal extension of the guard.

14 Claims, 2 Drawing Sheets

(56) References Cited

U.S. PATENT DOCUMENTS

| | | |
|---|---|---|
| 2002/0128625 A1 | 9/2002 | Tanaka et al. |
| 2003/0023213 A1 | 1/2003 | Fernfors et al. |
| 2004/0073180 A1 | 4/2004 | Strannemalm |
| 2004/0097893 A1 | 5/2004 | Elfstrom et al. |
| 2004/0162537 A1 | 8/2004 | Manasek |
| 2006/0025745 A1* | 2/2006 | Toro et al. .............. 604/385.101 |
| 2006/0282053 A1 | 12/2006 | Rohrl |
| 2010/0262111 A1* | 10/2010 | Lindstrom .............. 604/385.03 |

FOREIGN PATENT DOCUMENTS

| | | |
|---|---|---|
| GB | 2 304 586 | 3/1997 |
| WO | 91/07155 | 5/1991 |
| WO | 92/15269 | 9/1992 |
| WO | 98/29073 | 7/1998 |
| WO | 98/58613 | 12/1998 |
| WO | 99/51178 | 10/1999 |
| WO | 2004/004617 | 1/2004 |
| WO | 2006/062444 | 6/2006 |
| WO | 2009/074897 | 6/2009 |

\* cited by examiner

MALE INCONTINENCE GUARD COMPRISING AN ABSORBENT BARRIER

CROSS-REFERENCE TO PRIOR APPLICATION

This application is a §371 National Stage Application of PCT International Application No. PCT/SE2011/050822 filed on Jun. 22, 2011, which claims priority to PCT International Application No. PCT/SE2010/050731 filed on Jun. 24, 2010, both of which are incorporated herein in their entirety.

TECHNICAL FIELD

The present disclosure relates to a male incontinence guard including a liquid permeable topsheet, a backsheet, and an absorbent body between the topsheet and the backsheet. The incontinence guard has a transverse (x) direction and a longitudinal (y) direction and is divided by a transverse dividing line into a front region with a front transverse edge and a rear region with a rear transverse edge. The front region has a greater maximum extension in the transverse direction than the maximum extension of the rear region in the transverse direction, and the longitudinal extension of the rear region is 10-60% of the longitudinal extension of the guard.

BACKGROUND

Light incontinence is a large and hidden handicap which causes sufferers to involuntarily leak urine. Although referred to as light incontinence in teems of the amount of urine leakage, the discomfort experienced by the person affected may be significant. Light incontinence is a well recognized problem among women, and there is a large variety of female incontinence guards to choose from. However, a large group of men also suffer from light incontinence, especially those with prostate problems. Following surgery, these men are usually afflicted by drip incontinence, which causes a great deal of suffering.

It is known that there is a large group of men who have not sought care for their incontinence problems and whose problems are not related to previous surgery. The size of this group is not known, but studies in certain countries show that light incontinence is a very widespread problem.

Due to the anatomical differences between men and women, and the differences in the nature of the incontinence, female incontinence guards are not suitable for male users. Furthermore, incontinence guards intended for heavy incontinence are unnecessarily large and uncomfortable to wear.

For this reason, male incontinence guards having a more discrete appearance have been designed. Such an incontinence guard typically comprises an absorbent body which tapers towards one end from a front portion of the article to a crotch portion of the article; i.e. it has an essentially triangular shape. When the incontinence guard is used, the wider front end portion is intended to be directed forwards in the direction of the abdomen area of the wearer, and the narrower rear end portion is intended to be directed backwards and extend a little way below the genitals of the wearer.

One example of such a construction is described in WO 91/07155, wherein the absorbent body is enclosed in a covering consisting of a liquid permeable top layer and a liquid impermeable bottom layer. The incontinence guard of this publication is provided with elastic threads or the like, which are applied with pretensioning to the covering on both sides of the absorbent body and which converge in the direction of the narrower end portion of the absorbent body.

One disadvantage of the construction according to WO 91/07155 is that undesirable folds extending from the absorbent body in the lateral direction can lead to urine leakage along the folds out of the article.

Several attempts have been made to solve the problem of lateral leakage towards the crotch region of the user. For example, WO 2006/062444 discloses a guard having the tapered construction described above and comprising an elastic element attached to the liquid-permeable surface layer along at least parts of the longitudinal side edges of the article, which element comprises an elastic material piece. A cut in the form of a slit or cutout is arranged between the attachments, and the cut extends from a front edge of the elastic element in the direction of a rear edge to an end point of the cut. A pocket intended to receive urine leaking in the lateral direction is thereby formed between the elastic element and the liquid-permeable surface layer.

Furthermore, the provision of elastic means along the longitudinal edges of the male hygiene article is disclosed in e.g. WO 1992/015269, EP 0 167 931 and EP 0 091 412. The elastic means provide a basin-like like configuration to at least partly surround the scrotum and to prevent lateral leakage.

Although the elastic elements of these publications or the pocket formed in WO 2006/062444 prevent lateral leakage, these means only act as physical barriers to prevent the most immediate discharge of urine. Furthermore, pre-tensioned elastic gather cover materials along the edges of the guard imparts a wrinkled, irregular diaper-like appearance, which may be regarded by the wearer as uncomfortable and may give rise to chafing. Hence, there is a need in the art to provide a male incontinence guard which is comfortable to wear and which provides for an efficient and more reliable prevention of urine leakage in the lateral direction.

SUMMARY

It is desired to fulfil the above mentioned need and to provide a discrete, comfortable and efficient male incontinence guard suitable for men with light incontinence. Furthermore, the guard should be capable of preventing leakage of urine in the lateral direction.

A first aspect relates to a male incontinence guard including a liquid permeable topsheet, a backsheet, and an absorbent body between the topsheet and the backsheet. The guard has a transverse (x) direction and a longitudinal (y) direction and is divided by a transverse dividing line into a front region with a front transverse edge and a rear region with a rear transverse edge. The front region has a greater maximum extension in the transverse direction than the maximum extension of the rear region in the transverse direction and the longitudinal extension of the rear region is 10-60% of the longitudinal extension of the guard. Furthermore, an absorbent barrier including at least one first superabsorbent material is arranged to follow the contour of at least the rear region.

The absorbent barrier is arranged at the narrower end section of the guard; i.e. the rear region of the guard, where leakage of urine is most critical. The superabsorbent material present in the barrier absorbs urine emitted by the user and prevents leakage towards the crotch region of the user.

The absorbent barrier may include a first and a second elongate absorbent element. The elongate absorbent elements have first ends that are directed towards the front transverse edge of the male incontinence guard and second ends that are located in the rear region of the incontinence guard. The elongated absorbent elements may extend from the rear region of the incontinence guard into the front region of the incontinence guard or may be completely located in the rear region of the incontinence guard with both the first and the second ends of the elongated absorbent elements located in the rear region of the incontinence guard.

The elongate absorbent elements are arranged in a generally V-shaped or U-shaped configuration following the contour of the incontinence guard and with the second ends of the elongate absorbent elements arranged in an overlapping configuration in the rear region of the incontinence guard. In this manner, a thickened absorbent portion is formed inward of the rear transverse edge in the rear region of the incontinence guard. The thickened absorbent portion provides the incontinence guard with increased absorbency and enhanced leakage protection at the rear end of the guard. The thickened absorbent portion of the absorbent barrier will also render the end portion more resistant to bending than adjacent thinner portions of the guard and will thereby increase shape stability of the narrow rear end of the incontinence guard.

The absorbent barrier may be an integral part of an absorbent body or may constitute the whole absorbent body. Alternatively, the absorbent barrier may be a component that is separate and distinct from a main absorbent body of the incontinence guard. As used herein, a main absorbent body of the male incontinence guard is an absorbent element of the incontinence guard that is designed such that it will absorb a majority, i.e. more than 50%, of the liquid that is captured by the guard. When a main absorbent body is present together with an absorbent barrier, the main absorbent body may be an absorbent layer that is placed beneath the absorbent barrier between the absorbent barrier and the backsheet and such that the absorbent barrier protrudes from the surface of the main absorbent body.

The longitudinal extension of the rear region may be 10-60%, e.g. 20-50% of the longitudinal extension of the guard. The absorbent barrier is thus arranged to follow the contour of the region of the article, where lateral leakage of urine most often occurs, and where the barrier serves its purpose most optimally.

The first superabsorbent material may be a superabsorbent polymer (SAP). Such superabsorbent polymers provide for an efficient absorption of urine, and have the ability to absorb at least about 10 times their own weight. In embodiments, the first superabsorbent material or SAP is in the form of a foam. An advantage using such superabsorbent foam material is that the material is soft and flexible. Furthermore, such a SAP foam expands heavily upon contact with water. At the expansion, the free volume of the material is increased, leading to that such superabsorbent material can receive a large amount of liquid under a short period of time.

The absorbent barrier may further include at least one second absorbent or non-absorbent material in addition to the first superabsorbent material. This is to either further enhance the absorptive capacity of the barrier and/or to create a physical barrier being raised above the surface of the backsheet or of a fluid acquisition/distribution layer when the absorbent barrier is the only absorbent body in the incontinence guard or being raised above the surface of a main absorbent body which serves to prevent urine from leaking towards the crotch region of the user.

The second absorbent or non-absorbent material may be any absorbent material which is resiliently compressible in the z-direction (thickness direction), such that when the wearer moves, sits down or stands up, the seal provided by the contact between the barrier and the wearer will be maintained throughout the wearing period. For example, the second absorbent material may be cellulosic fluff pulp. The first superabsorbent material and the cellulosic fluff pulp may be provided in the form of a mixture of cellulosic fluff pulp fibers and particulate superabsorbent material. With particulate superabsorbent material in this context meaning any kind of superabsorbent particles, granules, fibres, foam pieces, etc. that can be mixed with the cellulosic fluff pulp.

As mentioned above, when the absorbent barrier is a separate element provided in addition to a main absorbent body, it is typically placed directly on the main absorbent body and is raised above the level of the main absorbent body. When the absorbent barrier is the only absorbent body in the incontinence guard or when it is placed on an intervening layer between a main absorbent body and the topsheet, it may be in direct contact with an underlying layer such as a backsheet or a liquid acquisition/transport layer and may be raised above the level of the underlying layer. For instance, the absorbent barrier may have a height of from 2 to 20 mm above the level of the main absorbent body or other underlying layer. The height of the absorbent barrier may be different in different parts of the barrier such that the barrier has a non-uniform height. Furthermore, the absorbent barrier may have a uniform or non-uniform width of from 5 to 40 mm. An absorbent barrier having these dimensions allows for a reliable protection against leakage of urine both laterally and rearwards; i.e. towards the rear transverse edge. Furthermore, such a barrier provides superior comfort and fit, and the male genitals are held securely in place during use.

In particular embodiments, the backsheet is breathable so as to allow vapour to escape from the absorbent barrier and absorbent body, while still preventing liquids from passing there through.

These and other aspects of the invention will be apparent from and elucidated with reference to the embodiment(s) described hereinafter.

DETAILED DESCRIPTION OF PREFERRED EMBODIMENTS

In the following, embodiments of the invention will be described in further detail with reference to the illustrative figures attached hereto.

Figure 1:
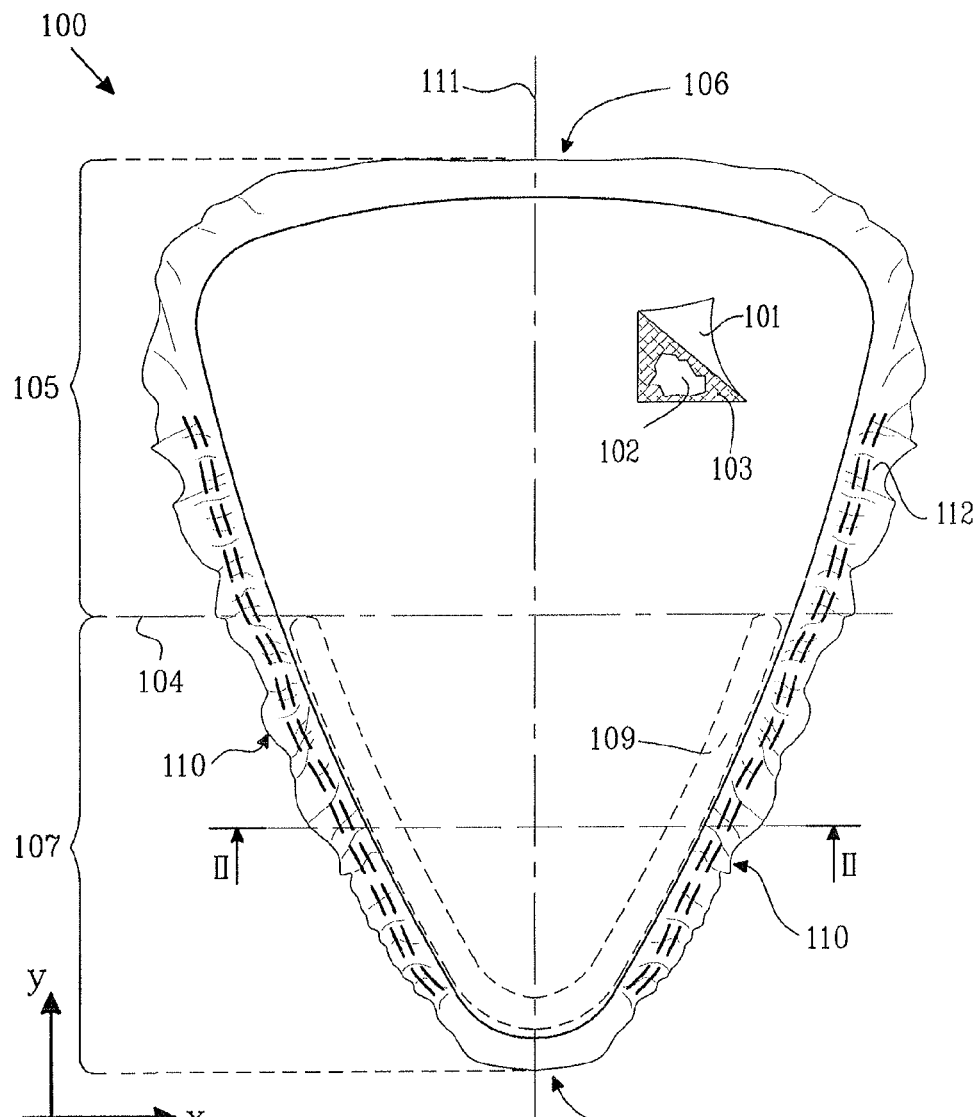
FIG. 1 illustrates a first male incontinence guard according to an embodiment of the invention seen from the liquid permeable top sheet.

FIG. 1 illustrates a male incontinence guard 100 according to an embodiment of the invention including a liquid permeable topsheet 101, a backsheet 102, and a main absorbent body 103 between the topsheet 101 and the backsheet 102. The guard has a transverse (x) direction and a longitudinal (y) direction and is divided by a transverse dividing line 104 into a front region 105 with a front transverse edge 106 and a rear region 107 with a rear transverse edge 108. The front region 105 has a greater maximum extension in the transverse direction than the maximum extension of the rear region 107 in the transverse direction. The longitudinal extension of the rear region 107 is 10-60% of the longitudinal extension of the guard. An absorbent barrier 109 including at least one superabsorbent material is arranged to follow the contour of at least the rear region 107.

The rear region 107 of the guard 100 is the region which is intended to be located rearwards on the wearer when the guard is worn, whereas the front region 105 is intended to be located forwards. As the maximum extension of the front region 105 in the transverse direction is greater than that of the rear region 107, the guard tapers slightly towards the rear region 107. The tapered shape allows the guard 100 to fit comfortably in the crotch region of the male user.

Hence, the guard 100 may have an essentially isosceles triangular shape or essentially isosceles trapezoid shape when fully extended in all directions. The term "essentially" in this context means that, for instance, the corners of the incontinence guard 100 may be rounded, or that the edges of the guard 100 may not be completely linear, but that the guard 100 has the general shape described herein.

The guard 100 typically includes side edges 110 extending between the front transverse edge 106 and the rear transverse edge 108. The side edges 110 have equal length and extend generally in the same direction as the longitudinal center line 111 through the guard 100. The front transverse edge 106 extends generally parallel to the transverse dividing line 104, transversely to the longitudinal center line 111 of the incontinence guard 100. The rear transverse edge 108 also extends generally transversely to the longitudinal center line 111 of the guard 100.

The rear region 107 may thus be defined on one side by the rear transverse edge 108, on two opposite sides by a portion of the side edges 110, and on the remaining side by the transverse dividing line 104 of the guard. The transverse dividing line 104 is an imaginary line that defines the longitudinal extension of the front region 105, and the rear region 107.

The rear region is further defined in that its longitudinal extension should be 10-60% of the longitudinal extension of the guard.

The front region 105 may thus be defined on one side by the front transverse edge 106, on two opposite sides by a portion of the side edges 110 and on the remaining side by the transverse dividing line 104. The front region 105 has a longitudinal extension of 40-90% of the longitudinal extension of the guard.

The guard 100 is symmetric about a longitudinal centre line 111, i.e. an imaginary line centred between the rear 108 and front 106 transverse edges, and the longitudinal extension; i.e. the length of the guard 100 may be between 10 and 30 cm, e.g. between 20 and 25 cm. The width of the guard 100 is measured along a transversal line where the article has its maximum transverse extension. This need not be the transverse dividing line 104. The width may be between 12 and 22 cm. It should be noted that these dimensions are merely indicative and not limitative.

Since leakage of urine is most critical at the narrower end of the guard; i.e. the rear region 107, an absorbent barrier 109 is arranged to follow the contour of at least the rear region 107. Hence, the barrier 109 is arranged to follow the contour of the rear transverse edge 108 and to extend along at least part of the side edges 110. This does not exclude the case when the barrier extends along the complete length of the side edges 110.

The superabsorbent material present in the absorbent barrier 109 absorbs and retains urine emitted by the user and prevents leakage towards the crotch region of the user.

The present inventors have performed experiments to see where lateral leakage is likely to occur. First, a plurality of used (test users) incontinence guards were analyzed. In this investigation, the area of the absorbent body was divided into a plurality of squares having a side length of 10 mm. Subsequently, the used products were visually analyzed to determine which squares contained urine. In this study, lateral leakage of urine was most prominent in the squares along the side edges of the rear region; i.e. up to a longitudinal extension of about 60%, typically 20-50%.

Accordingly, the absorbent barrier 109 should be arranged to follow the contour of this region of the guard 100.

Furthermore, when the wearer of the incontinence guard is active; i.e. walks, runs or is in a standing position, leakage of urine may also occur rearwards; i.e. towards the rear transverse edge 108. Therefore, the absorbent barrier should be arranged to follow the contour of the rear transverse edge. The absorbent barrier 109 including at least one first superabsorbent material is thus arranged to absorb urine leaking both laterally and rearwards.

As used herein, the term "superabsorbent material" refers to a water-swellable, water-insoluble organic or inorganic material capable of absorbing at least about 10 times its own weight as according to ISO 17190-6 "Gravimetric determination of fluid retention capacity in saline solution after centrifugation".

Materials suitable for use as super absorbent materials in the absorbent barrier 109 include, without limitation, natural materials such as polysaccharides, polypeptides and the like, as well as synthetic materials such as synthetic hydrogel polymers. Typically a superabsorbent polymer (SAP) is used as the first superabsorbent material. Examples of SAP materials include e.g. alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are typically crosslinked to render the material substantially water insoluble.

The absorbent barrier may include at least 10%, e.g. at least 20% by weight of the superabsorbent material, calculated on the total weight of the absorbent barrier 109 in a dry condition. Thereby, a high absorption capacity and a high liquid storing capacity may be achieved. It is also conceivable that the absorbent barrier 109 fully consists of the first superabsorbent material.

Since the absorbent barrier 109 should be capable of quickly accommodating liquid leaking towards the crotch region, the first superabsorbent material preferably has a high instantaneous fluid absorption capacity. A superabsorbent material, which can absorb 5 grams of bodily fluids per gram superabsorbent material in 10 seconds, is usually defined as a fast super absorbent material. An example of a fast liquid-absorbing superabsorbent material is a particulate superabsorbent material having a small particle size; i.e. a low particle diameter. Such a particulate superabsorbent material may exhibit an average particle size of between 150 μm and 400 μm.

The super absorbent materials may be in any form suitable for use in absorbent composites including particles, fibers, flakes, spheres, foam, and the like. Furthermore, the super absorbent materials may be slightly surface crosslinked.

The first superabsorbent material may be in the form of a foam; e.g. a polyacrylate based foam material. A polyacrylate-based foam material may be produced by the saturation under pressure using carbon dioxide of a solution, which at least contains monomer, a cross-linking material, an initiator and a tenside in a vessel during stirring. When the solution is removed from the vessel through a nozzle, the solution is expanded and a foamed structure is achieved. The foamed structure is then locked in that polymerisation and cross-linking are initiated by for instance UV radiation and/or e-beam radiation. Finally, the material is compressed and dried.

The foam material may also be a viscose foam, i.e. a compressed foam material including regenerated cellulose.

The absorbent barrier 109 may further include at least one second absorbent or non-absorbent material. Hence, the absorbent barrier 109 may include a mixture of the first superabsorbent material and a second absorbent material, which may be a material selected from the above mentioned list of materials suitable as the first superabsorbent material. The second absorbent material may have different properties in terms of liquid acquisition capacity, liquid distribution capacity and storage capacity. In this respect, the absorption capacity of the absorbent barrier 109 is further improved.

Typically, the second absorbent or non-absorbent material is a material which is resiliently compressible in the z-direction or thickness direction such that it will at least to some degree regain its uncompressed extension in the z-direction after having been subjected to a z-direction force such as arising under normal wearing conditions such as when the wearer is sitting down. In particular embodiments, the second absorbent or non-absorbent material of the absorbent barrier 109 is resilient both under wet and dry conditions. The absorbent barrier 109 will thus change its height as the wearer moves, sits down or stands up so that the seal provided by the close contact between the barrier 109 and the wearer will be maintained throughout the wearing period.

The second absorbent material may be cellulosic fluff pulp, which may be compressed or have a layered structure, or it may be a foam material, e.g. an open porous foam material. Other suitable materials are fluffy nonwoven, rolled nonwoven sheets, which may be regarded as absorbent or non-absorbent depending on the fibres of the nonwoven. For example, the absorbent barrier 109 may include a non-absorbent fiber structure or wadding containing the first superabsorbent material.

The purpose of the second absorbent or non-absorbent material in this regard is mainly to improve the barrier properties and prevent lateral and rearwards liquid flow, but also to provide comfort to the wearer.

Typically, the absorbent barrier 109 includes a mixture of cellulosic fluff pulp and the first superabsorbent material, e.g. a superabsorbent polymer. Depending on the amount of cellulosic fluff pulp in the barrier 109, the amount of superabsorbent material may be adjusted.

Figure 2:
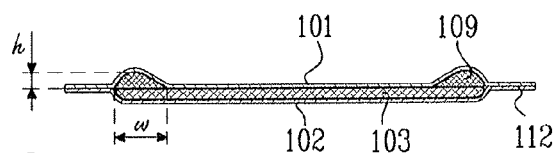
FIG. 2 is a cross-sectional view along the transversal line II-II in FIG. 1.

As illustrated in FIG. 2, the absorbent barrier 109 is typically raised above the level of the absorbent body 103. Hence, the absorbent barrier 109 has dual functions of keeping the guard 100 securely in position against the body of the wearer of the guard 100 and of providing a gasketing seal against rearwards and lateral leakage of urine.

The absorbent barrier 109 may have a height, h, of from 2 to 20 mm at zero load when measured in dry condition, such that the barrier is raised above the level of the absorbent body 103. The term "height" means the thickness of the barrier 109 in the z direction. Typically, the height is from 5-15 mm, e.g. 5-10 mm.

Furthermore, the absorbent barrier 109 may have a width of from 5 to 40 mm at zero load when measured in dry condition. The term "width" means the extension of the barrier 109 in the transverse direction. Typically, the width is in the range of from 10-30 mm, e.g. 10-20 mm.

These dimensions provide an absorbent barrier 109 which efficiently prevents urine from leaking towards the crotch region. Furthermore, a barrier having these dimensions allows for a superior comfort and fit, and the male genitals are held securely in place during use.

The absorbent barrier 109 may be arranged between the absorbent body 103 and the topsheet 101, as illustrated in FIG. 2. Hence, during manufacturing, the barrier 109 may be applied on the absorbent body 103, and subsequently, the topsheet 101 may be arranged thereupon.

The backsheet 102 is typically liquid-impermeable and may include a plastic film, e.g. a polyethylene or polypropylene film, a non-woven material treated with e.g. a liquid impervious material or a hydrophobic non-woven material which resists liquid penetration, or a laminate including plastic films and nonwoven materials. Other types of liquid impermeable materials could also be used, such as closed-cell plastic foams or various liquid barrier laminates. In particular embodiments, the backsheet is permeable to air and vapour so as to allow vapour to escape from the absorbent body, while still preventing liquids from passing there through.

Hence, in particular embodiments, the backsheet 102 is breathable. Examples of breathable backsheet materials are porous polymeric films, nonwoven laminates from spunbond and meltblown layers, laminates from porous polymeric films and nonwovens.

Another suitable design of the backsheet 102 is to use a laminate with a textile nonwoven outer layer giving a tailored appearance to the article such that there is a soft and non-sticky portion where the backsheet 102 may come into contact with the user's skin. The contact between the backsheet 102 and the user's skin may occur e.g. at edges in the crotch portion.

One preferred example of a suitable material for the backsheet 102 is a 25 g/m$^2$ nonwoven/plastic laminate from Trioplanex, available under the trade name W14Ma11. The backsheet 102 could also be made from renewable materials. Examples of such backsheets are Bio-Air, a plastic film commercially available from Nuova Pansac, and PLA/PP Bico 50/50, a non-woven material commercially available from Fiberweb.

The garment facing surface of the backsheet 102 may have at least one area of adhesive means (not shown). The adhesive means may be arranged so as to fix the guard to the garment (e.g. the underwear) of a user. The adhesive means may be applied in any continuous or intermittent way and geometrical pattern, e.g. rectangular, squared, oval, polygonal, circular, triangular etc. The adhesive means could be any kind of pressure-sensitive adhesive that is commercially available. Prior to use of the guard 100, the adhesive means is typically covered by a strip of release material. The release material acts to protect the adhesive means from dirt and damage and to prevent the adhesive means from adhering before the guard 100 is to be used. The single strip of release material could be made of kraft paper, calendered paper, or any other materials well-known in the art for such purposes. The face of the release material, which contacts the adhesive means could have a release coating, such as silicone, to easily facilitate the removal of the release material. Other types of fasteners, such as friction means or hook-type fasteners that mechanically attach to a users underwear may be used in addition to or instead of adhesive fasteners.

The topsheet 101 and the backsheet 102 of the male incontinence guard 100 typically have a somewhat greater extension in the x-y plane than the absorbent body 103, and extend along the whole circumference of the absorbent body 100. The topsheet 101 and the backsheet 102 may be connected to each other within the projecting portions thereof 112. Joining can occur by gluing, or by welding by means of ultrasound or a laser, or by mechanical joining, for example in the form of embossing or compression, etc. or by some other appropriate method of joining, for example by thermal bonding.

Considering that the liquid-permeable topsheet 101 is intended to be in direct contact with the user's body, the topsheet is preferably manufactured from a material that exhibits characteristics such as dryness and softness when the guard 100 is being worn. It is also desirable for the topsheet 101 to be non-irritating to the skin and to have a soft and textile-like surface which remains dry, even in the event of repeated wetting. The topsheet 101 may include a nonwoven material, e.g. a spunbond, carded, thru-air, spunlace (hydroentangled), meltblown, wetlaid nonwoven material, or a combination of these. The nonwoven material may be based on either natural fibres such as cellulose or cotton, or alternatively on synthetic fibres such as polypropylene (PP), polyethylene (PE) polyester (PET), polyamide (PA), or a combination of these. If a combination is used, this could be a mixture of fibres from different natural and/or synthetic polymers (for example PP/PE bi-component fibres or PP/PE copolymers), although each fibre can also contain different polymers.

The topsheet 101 may also include a perforated, hydrophobic nonwoven material in order to keep the surface which is closest to the user's body dry. The holes of the perforated, hydrophobic nonwoven material impart a textile-like and comfortable feel to the topsheet. The diameter of the holes of such a perforated, hydrophobic nonwoven material is typically larger than the distance between the fibres in the material such that liquid can be led down through the holes in the topsheet 101 to the subjacent absorption body 103. The skilled person is able to understand how the holes in the perforated, hydrophobic nonwoven material may be adjusted depending on the intake properties and the type of absorbent article which is to be produced.

A laminate including two or more top sheet materials could also be used as the topsheet material.

One particular example of a suitable material for the topsheet is a 18 g/m² spunbond nonwoven from Union, available under the trade name 51800 PPW. The topsheet could also be made from renewable raw materials. An example of such a topsheet based on renewable raw materials is TERCOT 20, commercially available from Fiberweb.

The main absorbent body 103 may be made up of one or more layers of cellulose fluff pulp and may be of any conventional kind. The absorbent body 103 may contain fibers or particles of highly absorbent material, e.g. superabsorbent polymers (SAP). The superabsorbent polymers may mixed with cellulose fluff pulp and/or be arranged in pockets or layers in the absorbent body 103. The main absorbent body 103 may further incorporate components for improving the properties of the main absorbent body 103, such as binder fibers, liquid-dispersing materials, wetness indicators, liquid acquisition materials etc. as known in the art.

The superabsorbent material present in the main absorbent body 103 may have different properties in terms of liquid acquisition capacity, liquid distribution capacity and storage capacity compared to the superabsorbent material present in the absorbent barrier 109. Since the main absorbent body 103 is arranged to receive repeated wetting by the wearer, it may be advantageous to use a superabsorbent material having a slower rate of absorption. This is to prevent gel blocking and to allow for repeat wetting.

The superabsorbent may be applied in localised areas of a main absorbent body 103, e.g. in intake regions, liquid distribution regions and/or liquid retention regions. The person skilled in the art will understand how the concentration of SAP in an absorbent body may be adjusted depending on the absorbent properties and the type of absorbent article which is to be produced.

One particular example of a suitable material for the absorbent body 103 is pulp mixed with approximately 30% of SAP, such as SAP from BASF, Ludwigshafen, Germany available under the trade name Hysorb M7125. The mixture of cellulose fluff and SAP preferably has a density of 0.08-0.13 g/cm³.

The main absorbent body 103 may be made from, or include, a chlorine-free fluff pulp such as Totally Chlorine Free fluff pulp which is commercially available from Stora Enso.

The main absorbent body 103 may be constructed by several layers, such as a liquid acquisition layer, a storage layer and a distribution layer in order to fulfil the functions which are desired with an absorbent body; i.e. capacity to quickly receive liquid, distribute it within the body and store it.

A fluid acquisition layer is usually a so-called high loft material and may be produced by carding and through-air bonding or by needling of synthetic fibres, such as polyester, polypropylene or mixtures thereof. A suitable material for the acquisition layer is a hydrophobic wadding of through air nonwoven available from LIBELTEX, having the trade name DRY WEB T 23W.

It is to be understood that for incontinence guards for men suffering from light incontinence, the main absorbent body may be omitted and the absorbent barrier 109 may serve as the only absorbent body, optionally supplemented with a liquid acquisition and/or distribution material such as tissue, fibrous wadding, airlaid fibre webs, etc. as known in the art.

Figure 3:
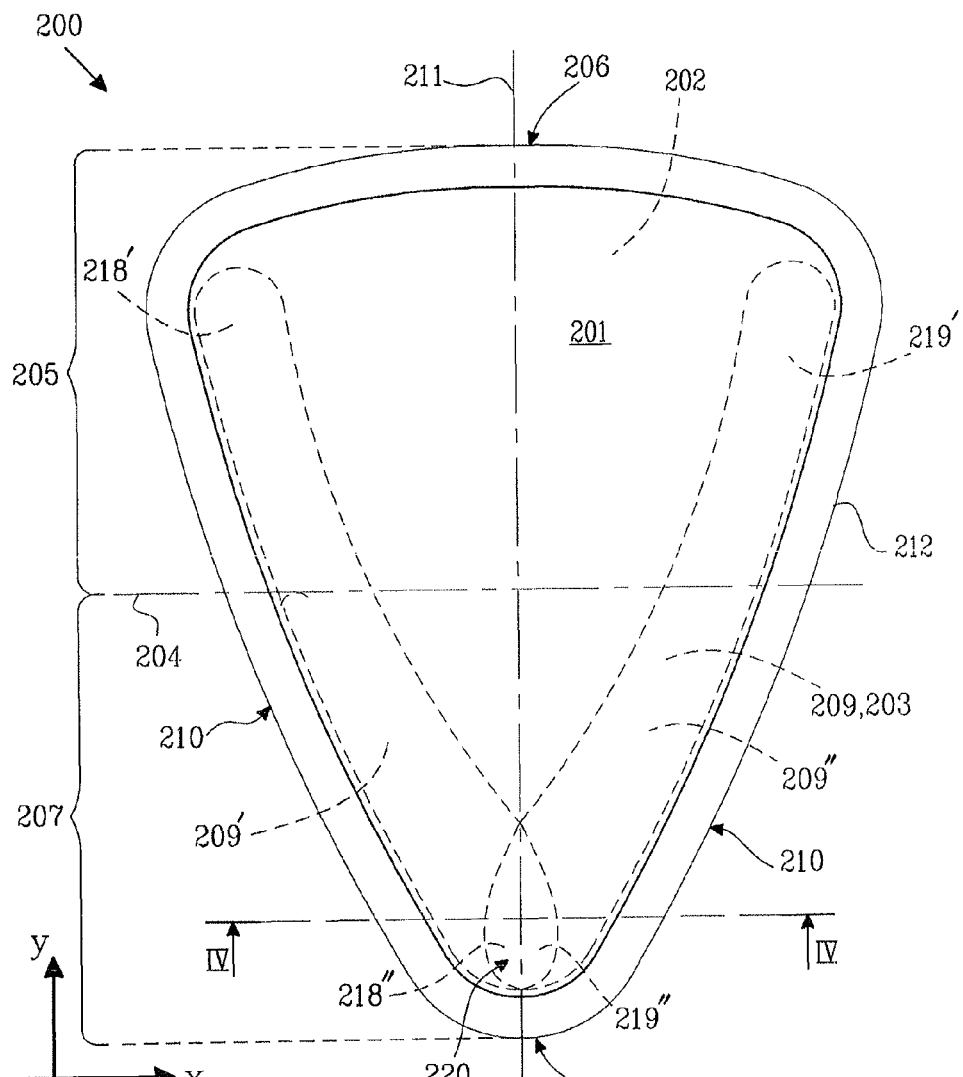
FIG. 3 illustrates a second male incontinence guard according to an embodiment of the invention seen from the liquid permeable top sheet.
Figure 4:
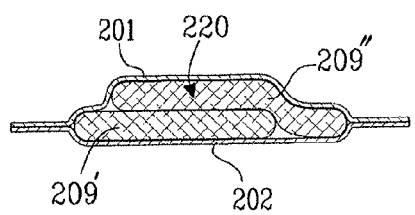
FIG. 4 is a cross-sectional view taken along the transversal line IV-IV in FIG. 3.

FIGS. 3 and 4 show a male incontinence guard 200 according to another embodiment of the invention. The male incontinence guard 200 in FIGS. 3 and 4 is similar in shape and construction to the male incontinence guard 100 in FIGS. 1 and 2 and corresponding elements have been numbered analogously. The male incontinence guard 200 includes a liquid permeable topsheet 201 and a backsheet 202 as set out above. The guard 200 has a transverse (x) direction and a longitudinal (y) direction and is divided by a transverse dividing line 204 into a front region 205 with a front transverse edge 206 and a rear region 207 with a rear transverse edge 208. As in the incontinence guard 100 in FIG. 1, the incontinence guard 200 has generally triangular shape such that the front region 205 has a greater maximum extension in the transverse direction than the maximum extension of the rear region 207 in the transverse direction. The longitudinal extension of the rear region 207 is 10-60% of the longitudinal extension of the guard.

An absorbent barrier 209 including at least one superabsorbent material is arranged to follow the contour of at least the rear region 207. The absorbent barrier 209 includes a first and a second elongate absorbent element 209', 209". The elongate absorbent elements 209', 209" have first ends 218', 219' directed towards the front transverse edge 206 of the male incontinence guard 200 and second ends 218", 219" located in the rear region 207. As is seen in FIGS. 3 and 4, the second ends 218", 219" of the elongate absorbent elements 209', 209" are arranged in an overlapping configuration and form a thickened absorbent portion 220 in the rear region 207 of the male incontinence guard 200. Although the male incontinence guard is shown with elongate absorbent elements 209',209" extending inward of the projecting portions 212 of the topsheet 201 and the backsheet 202 along the side edges 210 of the male incontinence guard 200 all the way to the front transverse edge 206, the elongate absorbent elements 209',209" may alternatively be shorter and may even be fully accommodated within the rear end region 207.

In the male incontinence guard 200 as shown in FIGS. 3 and 4, the absorbent barrier 209 constitutes the complete absorbent body 203. However, if additional absorption capacity is needed in the male incontinence guard 200, the absorbent barrier 209 may be supplemented with a separate absorbent body and/or a liquid acquisition/distribution structure. The supplementary absorbent body may be formed by any of the materials disclosed for the main absorbent body 103 in the incontinence guard 100 shown in FIGS. 1 and 2. Liquid acquisition and/or distribution materials may include tissue sheets, resilient porous fibre webs, etc., as known in the art.

The thickened portion 220 created by the overlapping rear ends 218", 219" of the elongate absorbent elements 209', 209" constitutes an enhanced barrier against rearward leakage. The thickened portion 220 may be placed behind the scrotum of a user of the incontinence guard 200 and may serve to hold the incontinence guard in place between the legs of the user. The thickened portion also serves as a stabilising reinforcement of the narrow rear region of the incontinence guard 200.

The absorbent barrier 209 in the male incontinence guard 200 may be made from any of the materials or combinations of materials disclosed of the absorbent barrier 109 in the FIGS. 1 and 2 incontinence guard 100. However, it may be preferred that the elongate absorbent elements 209', 209" making up the absorbent barrier 209 is made from a mixture of cellulose fluff pulp and superabsorbent material as set out herein.

Although the incontinence guard in FIGS. 3 and 4 is shown without elastic elements and without means for fastening of the incontinence guard to a user's undergarment, it is to be understood that elastic elements and fastening means are optional to all incontinence guards according to the invention.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. For example, the present invention is not limited to the use of a specific type of superabsorbent material as long as it fulfils the purpose of preventing lateral leakage. Furthermore, the dimensions of the guard, e.g. its length and width are not limitative, although the specified dimensions provide a satisfactory level of inconspicuousness and are particularly suitable for men demanding a high degree of discretion.

The invention claimed is:

1. A male incontinence guard comprising:
   a liquid permeable topsheet,
   a backsheet, and
   an absorbent body between said topsheet and said backsheet,
   wherein said guard has a transverse direction and a longitudinal direction and is divided by a transverse dividing line into a front region with a front transverse edge and a rear region with a rear transverse edge; said front region having a greater maximum extension in the transverse direction than the maximum extension of said rear region in the transverse direction, and wherein the longitudinal extension of said rear region is 10-60% of the longitudinal extension of said guard, and
   an absorbent barrier comprising at least one first superabsorbent material is arranged to follow the contour of at least said rear region and wherein said absorbent barrier comprises a first and a second elongate absorbent element, said elongate absorbent elements having first ends directed towards said front transverse edge and second ends located in said rear region and extending across a longitudinal centerline of said guard, said second end of the first elongate absorbent element overlapping said second end of the second elongate absorbent element.

2. A male incontinence guard according to claim 1, wherein said absorbent barrier constitutes said absorbent body.

3. A male incontinence guard according to claim 1, wherein the longitudinal extension of said rear region is 20-50% of the longitudinal extension of said guard.

4. A male incontinence guard according to claim 1, wherein said first superabsorbent material is a superabsorbent polymer.

5. A male incontinence guard according to claim 1, wherein said first superabsorbent material is in the form of a foam.

6. A male incontinence guard according to claim 1, wherein said absorbent barrier further comprises at least one second absorbent or non-absorbent material.

7. A male incontinence guard according to claim 6, wherein said second absorbent or non-absorbent material is cellulosic fluff pulp.

8. A male incontinence guard according to claim 7, wherein said first superabsorbent material and said cellulosic fluff pulp are provided in the form of a mixture.

9. A male incontinence guard according to claim 1, wherein said absorbent barrier is placed on an underlying layer of said incontinence guard, in direct contact with said underlying layer and is raised above the level of said underlying layer.

10. A male incontinence guard according to claim 9, wherein said absorbent barrier has a height above the level of said underlying layer of from 2 to 20 mm.

11. A male incontinence guard according to claim 1, wherein said absorbent barrier has a width of from 5 to 40 mm.

12. A male incontinence guard according to claim 1, wherein said incontinence guard comprises a main absorbent body in addition to said absorbent barrier and wherein said absorbent barrier is arranged between said main absorbent body and said topsheet.

13. A male incontinence guard according to claim 1, wherein said backsheet is breathable.

14. A male incontinence guard according to claim 9, wherein said guard has a height above the level of said underlying layer that is greater in areas including said absorbent barrier than areas not including said absorbent barrier.

* * * * *